United States Patent [19]

Singleton et al.

[11] Patent Number: 4,689,472

[45] Date of Patent: Aug. 25, 1987

[54] CONTROL DEVICE FOR CORROSION TESTING APPARATUS

[75] Inventors: Raymund Singleton, 31653 Electric Blvd., Avon Lake, Ohio 44012; Lawrence J. Carmon, Jr., Rocky River, Ohio

[73] Assignee: Raymund Singleton, Avon Lake, Ohio

[21] Appl. No.: 752,448

[22] Filed: Jul. 5, 1985

[51] Int. Cl.$^4$ .................. H05B 1/02; G01N 17/00
[52] U.S. Cl. .................. 219/331; 219/328; 219/333; 137/409; 361/284
[58] Field of Search ......... 219/272, 273, 328, 331, 219/333, 322, 336; 137/409 X; 361/284

[56] References Cited

U.S. PATENT DOCUMENTS

| | | |
|---|---|---|
| 2,521,921 | 9/1950 | Kolar . |
| 3,063,432 | 11/1962 | Bond . |
| 3,116,977 | 1/1964 | Grabowski . |
| 3,557,819 | 1/1971 | Singleton . |
| 3,588,859 | 6/1971 | Petree .................. 361/284 |
| 3,594,128 | 7/1971 | Singleton . |
| 3,936,273 | 2/1976 | Powell . |
| 3,948,439 | 4/1976 | Heeger . |
| 4,083,038 | 4/1978 | Klebanoff .................. 361/284 |
| 4,201,085 | 5/1980 | Larson .................. 361/284 |
| 4,289,954 | 9/1981 | Brognano et al. .................. 219/333 |
| 4,354,094 | 10/1982 | Massey et al. .................. 219/333 |
| 4,480,173 | 10/1984 | Butterfield .................. 219/328 |

*Primary Examiner*—John Sipos
*Assistant Examiner*—Donald R. Studebaker
*Attorney, Agent, or Firm*—Fay, Sharpe, Beall, Fagan, Minnich & McKee

[57] ABSTRACT

A control device for a corrosion testing apparatus includes an airtight air saturation tower which is adapted to contain a liquid. A heater is provided in the tower to heat the liquid. A sensor is provided adjacent a wall of the tower, to sense an abnormal condition in the tower. The sensor can be adapted to measure the presence of liquid in the tower adjacent the sensor or the temperature of a wall of the tower. A control device is provided for shutting off the heater when the sensor detects an abnormal condition in the tower.

14 Claims, 4 Drawing Figures

CONTROL DEVICE FOR CORROSION TESTING APPARATUS

BACKGROUND OF THE INVENTION

This invention generally pertains to control devices. More specifically, the present invention relates to a control device which senses an abnormal condition and shuts down a heating device as a result thereof.

The invention is particularly applicable to a humidifying tower of a corrosion testing device and will be described with particular reference thereto. However, it will be appreciated by those skilled in the art that the invention has broader applications and may also be adapted for use in other types of devices.

Corrosion testing is required of many items which must meet corrosion resistance standards set by various governmental agencies and industrial concerns. The testing of the ability of various products to withstand corrosive influences such as salt vapor is frequently conducted by accelerated exposure techniques. These methods utilize a test cabinet into which parts to be tested are placed. A corrosive atmosphere, for example, salt vapor fog is introduced into the cabinet in specified amounts for specified periods of time. Exposed items are then removed from the cabinet and scrutinized for signs of corrosion, structural breakdown, and the like.

Generally, corrosion testing devices are compact, approximately the size of a home food freezer. Since there is not a great deal of excess space within the corrosion testing cabinet, feed mechanisms for feeding the corrosive gases and liquids to appropriate outlets on the cabinet are provided on the outside of the cabinet. Necessary adjuncts to the cabinet are an air saturation tower, a salt solution reservoir and two storage tanks to supply the liquid to the tower and reservoir.

The air saturation or "bubble" tower functions to give air introduced into the cabinet a uniform humidity. To accomplish this result, air is bubbled into the bottom of the saturation tower and passes through water to acquire the desired humidity. Saturated air is then drawn from the top of the tower and is introduced into an atomizing nozzle of a fog tower in the cabinet. A certain amount of water in the air saturation tower is evaporated by the air passing therethrough with the result that the level of the water within the tower is lowered. It is therefore necessary that a replenishing supply be connected to the tower to replenish the water therein.

Generally, a heater is provided in the bottom of the tower to heat the liquid contained therein. A temperature control is electrically connected to the heater to maintain the desired operating temperature in the tower. However, if the temperature control malfunctions raising the temperature of the tower or if for some reason such as a leaky water delivery line, an empty water reservoir, or operator neglect, the water level in the tower should be insufficient, the tower, which is generally made from a transparent plastic material for easy visual inspection, may be damaged due to heating. In other words, the tower may possibly melt due to overheating and the remaining contents thereof leak out onto the floor.

Accordingly, it has been considered desirable to develop a new and improved control device for corrosion testing apparatus which would overcome the foregoing difficulties and others while providing better and more advantageous overall results.

BRIEF SUMMARY OF THE INVENTION

In accordance with the present invention, a new and improved control device is provided for an air saturation tower of a corrosion testing apparatus.

More particularly in accordance with the invention, the control device includes an airtight air saturation tower which is adapted to contain a liquid. A heater is provided in the tower to heat the liquid. A sensor means is provided adjacent a wall of the tower for sensing the presence of liquid in the tower. A control means is provided for shutting off the heater when the sensor means detects the absence of liquid in the tower.

In accordance with another aspect of the invention, an over-temperature control device is provided for an air saturation tower of a corrosion testing apparatus.

More particularly in accordance with this aspect of the invention, the device includes an airtight air saturation tower which is adapted to contain a liquid. The tower has a bottom wall and side walls. A heater extends upwardly in the tower from the bottom wall thereof to heat the liquid. A temperature sensor which is responsive to the temperature of an adjacent tower wall is adapted to signal when the wall temperature becomes excessive. The temperature sensor is electrically connected to the heater whereby if the wall temperature becomes excessive, the heater will be automatically disconnected.

According to another aspect of the invention, a control device is provided for an air saturation tower of the corrosion testing apparatus.

In accordance with this aspect of the invention, the device includes an airtight air saturation tower having a liquid contained therein. A heater is provided in the tower to heat the liquid therein. A temperature control is provided for controlling the normal operation of the heater. A sensing device is positioned adjacent a wall of the tower and is disposed to sense an abnormal condition in the tower. A safety shut down warning means is associated with the sensing device. A switching means is electrically connected to the sensing device and to the safety shut down warning means to actuate the latter when the switching means de-energizes the heater due to a signal sent by the sensing device.

One advantage of the invention is the provision of a control device for an air saturation tower of a corrosion testing apparatus or the like.

Another advantage of the invention is the provision of such a device in the form of a proximity sensor, that is, a sensor which reacts to the proximity of an actuating means without physical contact or connection therewith. The sensor can be a liquid detecting sensor which senses the presence of liquid in the tower. Such a liquid detecting sensor can be in the form of a sonic sensor, a photoelectric sensor or it can work on inductive or capacitive principles.

Still another advantage of the present invention is the provision of such a sensing device in the form of a temperature sensor which senses an over-temperature condition of a wall of the tower.

Yet another advantage of the present invention is the provision of such a device on a holder which can be selectively moved up and down along the height of the tower.

Still yet another advantage of the present invention is the provision of a sensor which has a first power and a heater which has a second, separate, power supply.

Yet still another advantage of the present invention is the provision of a sensor electrically connected to a safety shut down warning light and a switching device so that when the sensor directs the switching device to shut off the heater, the safety shut down warning light illuminates.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENTS

Figure 1:
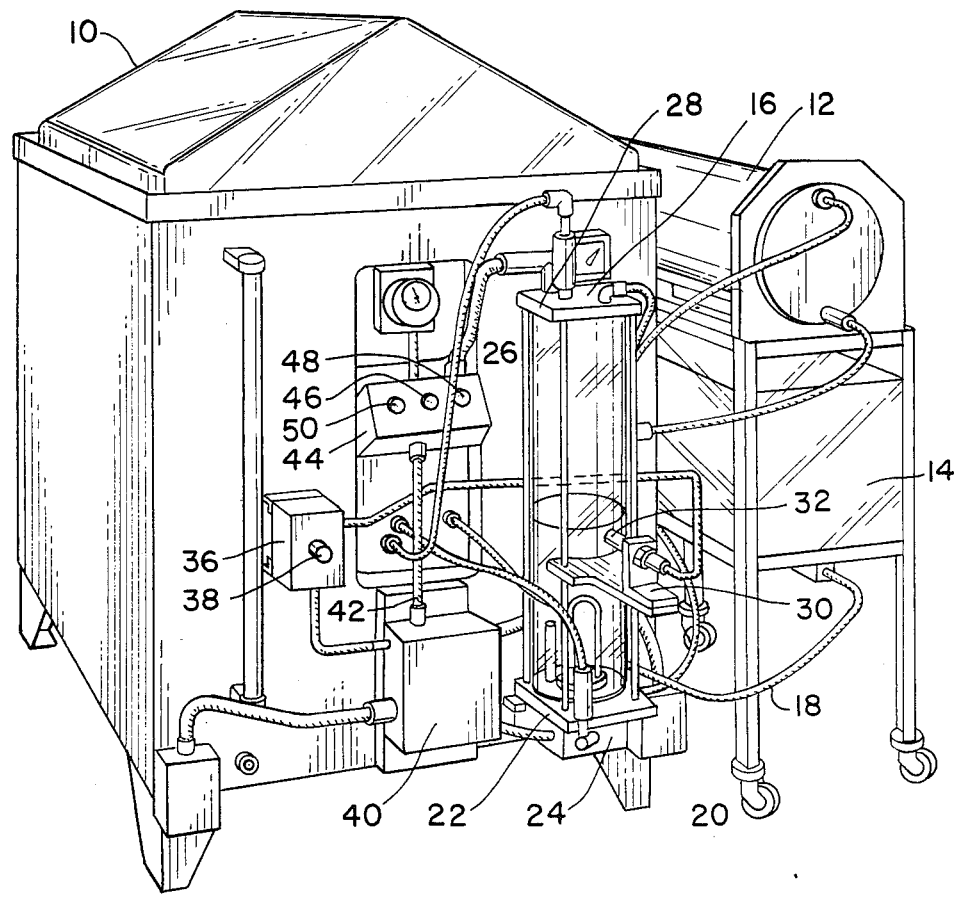
FIG. 1 is a perspective view of a corrosion testing apparatus including an air saturation tower which is provided with a sensing device according to the present invention and an associated cabinet.

Referring now to the drawings wherein the showings are for purposes of illustrating preferred embodiments of the invention only and not for purposes of limiting same, FIG. 1 shows a corrosion test assembly which employs a control device according to the present invention. While the control device is primarily designed for and will hereinafter be described in connection with the corrosion testing device, it will be appreciated that the overall inventive concept involved could be adapted for use in other environments as well.

More particularly, the corrosion testing device includes a completely enclosed testing cabinet 10 as well as an upper liquid storage tank 12 and a lower liquid storage tank 14. One of these storage tanks contains plain water and the other one contains a salt solution of the type dictated by the type of corrosion test which is to be run. An airtight air saturation tower 16 is preferably secured to a front side of the cabinet 10. Although a round tower 16 is illustrated, any other conventional shape of tower could also be used. The tower 16 is transparent for easy visual inspection as well as the purposes described hereinbelow. A plurality of fluid conduits 18 extend between the upper and lower liquid storage tanks 12, 14, the air saturation tower 16 and the cabinet 10.

Figure 2:
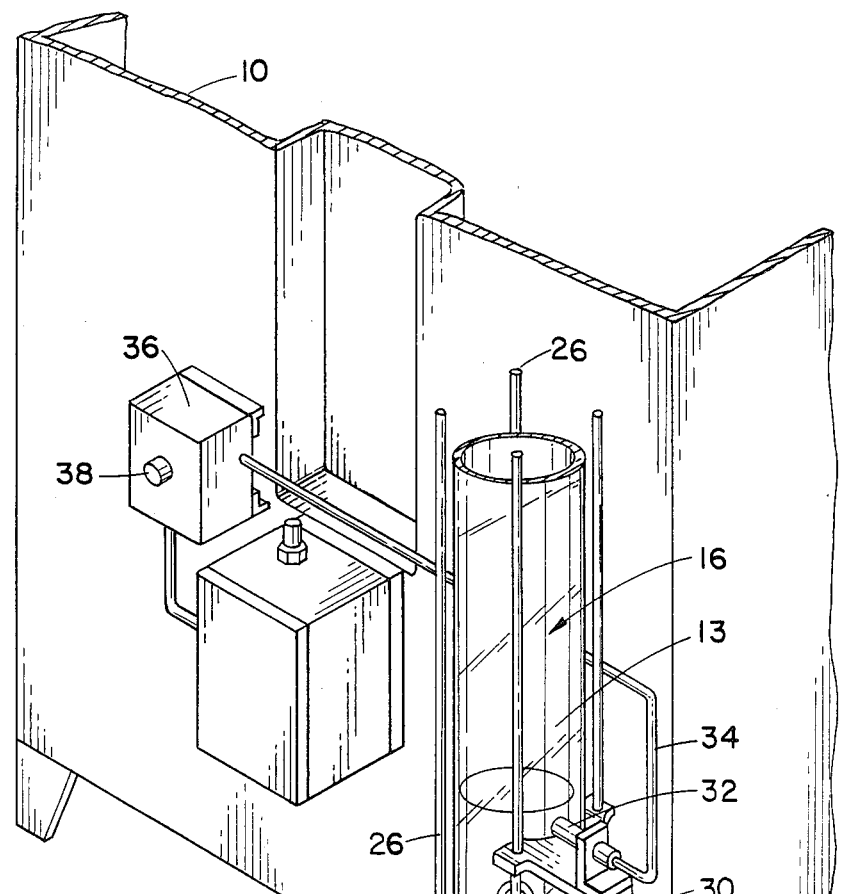
FIG. 2 is an enlarged schematic perspective view of the sensing device, and a portion of the tower and the associated cabinet of FIG. 1.

With reference now also to FIG. 2, the tower 16 extends substantially vertically along side the cabinet 10 and a heater element 20 extends upwardly within the tower 16 from a base plate 22 thereof. A heater junction box 24 is secured to the base plate 22 defining the bottom of the tower and is provided with a conventional control means to control the normal operation of the heater element 20. A plurality of tie rods 26 extend upwardly from the tower base plate or bottom plate 22 to a top plate 28 defining the upper end of the tower. Preferably, four tie rods 26 are provided one adjacent each corner of the top and bottom plates 22, 28. Also provided in the tower 16 is an air inlet 29 which allows air to bubble through the liquid in the tower.

A mounting bracket 30 is preferably slidably secured in any convenient conventional manner to two of the tie rods 26 and is adapted to hold a sensor element 32. The sensor 32 may be slidably mounted either on the front two tie rods of the tower 16, as illustrated in FIG. 1, or on a side two tie rods of the tower, as illustrated in FIG. 2. Of course, the mounting bracket could be configured to slide on only one of the tie rods 26, if desired. Also, more or less than the illustrated four tie rods 26 could be provided as desired.

As mentioned the sensor element 32 can be a thermal sensor for sensing the temperature of wall 33 of the tower 16 or a proximity sensor which senses the presence of water in the tower.

The proximity sensor, which generally senses whether the water level in the tower is above or below the position of the sensor, can be a sonic sensor, a photoelectric sensor or an inductive or capacitive type sensor. One suitable sensor is manufactured by Omron Tateisi Electronics Company of Kyoto, Japan and is sold as Model No. E2HM41. Such a sensor may have a detecting distance of approximately 1 to 25 mm and sense the presence or absence of water adjacent the sensor. In order for the proximity and photoelectric sensors, at least, to work the tower must be made of a transparent non-metallic material which may be a suitable type of plastic. As mentioned, a transparent tower is also advantageous for ease of visual inspection.

Another type of sensor which can be used is a temperature sensor for sensing the temperature of the wall 33 of the saturation tower 16. The sensor can be of the type which signals when it senses an over-temperature condition, such as the tower wall temperature being above approximately 160° F. (71° C.). Such a thermal sensor 32 is in contact with the tower wall 33 and is electrically connected to the heater so that when the sensor signals an over-temperature condition, the heater will be disengaged. This type of sensor can be in the form of a thermal probe known as a "snap disk" thermostat which is manufactured, for example, by the Thermo-O-Disc Company of Mansfield, Ohio.

A first wiring conduit 34 extends from the sensor 32 to a control means 36 which is preferably secured to the cabinet 10. A manual reset button 38 is provided on the control means 36 for resetting the heater element 20 once it is disconnected due to the action of the sensor element 32. A contactor enclosure 40 is electrically connected to the control means 36.

A second wiring conduit 42 electrically connects the contactor enclosure 40 with a control panel 44. Mounted on the control panel 44 is a cabinet pilot light 46, by which it can be determined whether the entire device is on and a tower pilot light 48. A fused on-off power switch 50 can be mounted on the panel 44 adjacent the cabinet and tower pilot lights to energize the cabinet 10 and the tower 16.

Figure 3:
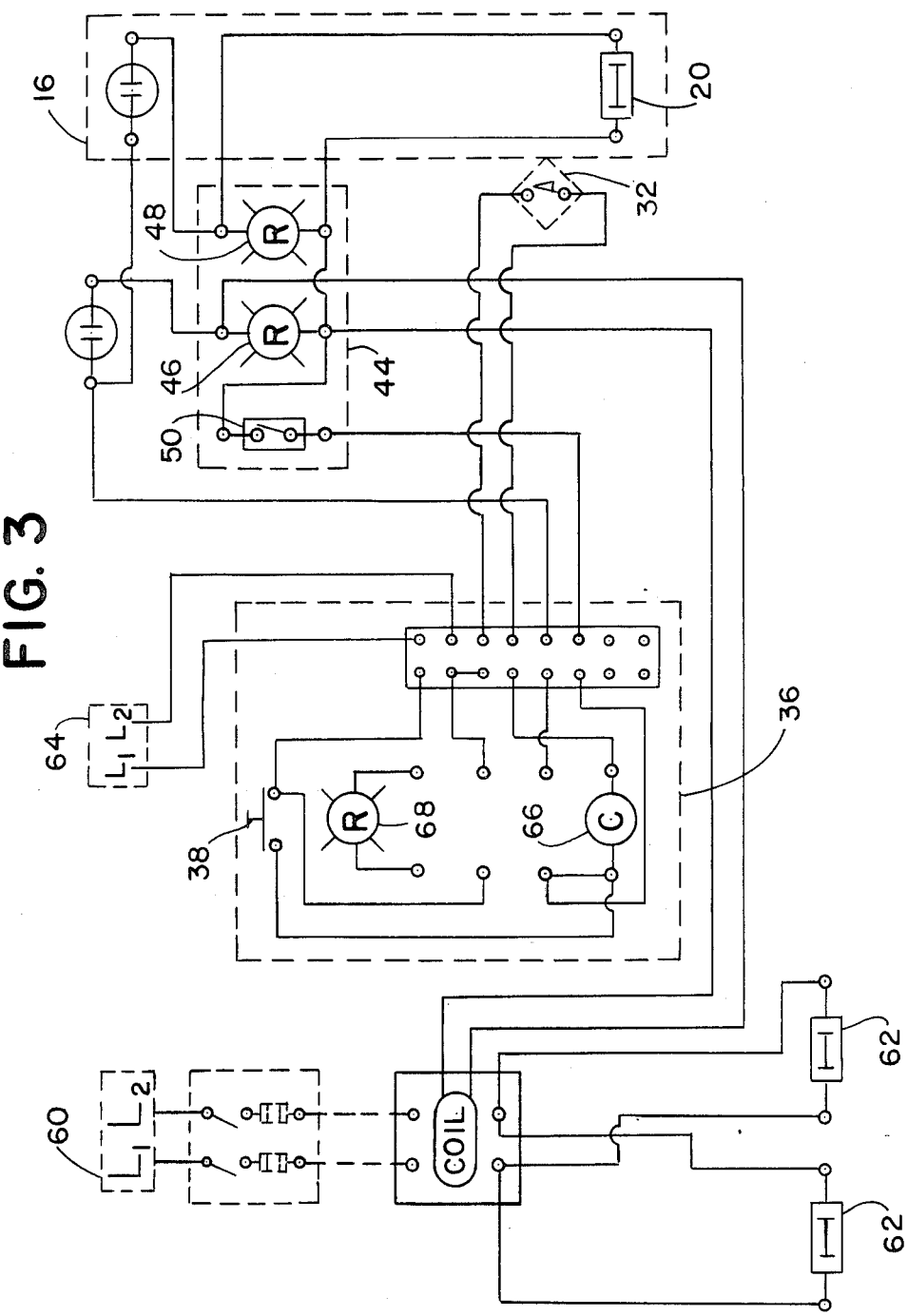
FIG. 3 is a wiring diagram of the sensing device, the tower and the associated cabinet of FIG. 1.

With reference now also to FIG. 3, a first electrical supply 60 is provided for the cabinet and is adapted to power a pair of cabinet heaters 62. A separate second electrical supply 64 is, however, provided for the saturation tower heater element 20, the sensor 32 and also powers the control means 36. The control means 36 includes a switching means in the form of a relay coil 66 and the requisite electrical hardware to allow power to energize the sensor 32. The control means 36 also includes the reset button 38 and a safety warning means in the form of a reset light 68. The reset light 68 can also be associated with the reset button 38, if desired, such as by having the button illuminated only when power is not provided to the heater 20.

Figure 2A:
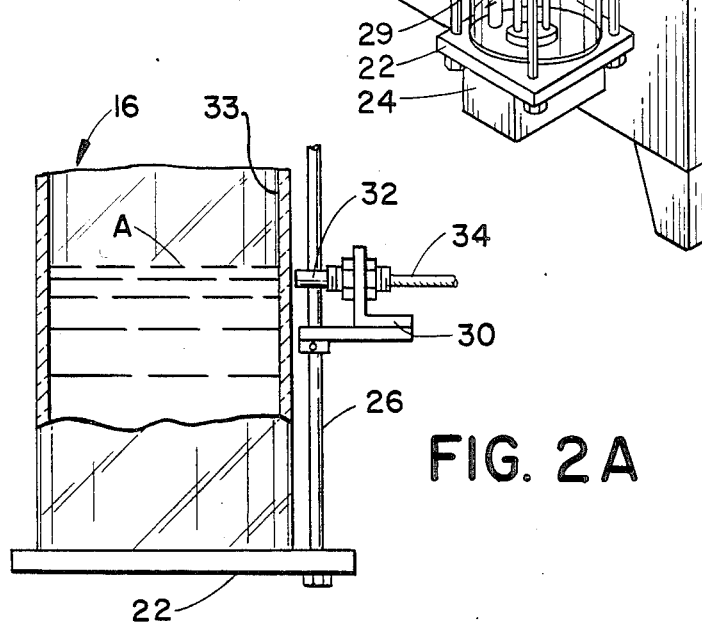
FIG. 2A is an enlarged side elevational view, in partial cross-section, of a portion of the tower and the sensing device of FIG. 2.

With reference now also to FIG. 2A, the sensor 32 can, in one embodiment, sense the presence or absence of liquid adjacent the sensor. If the fluid level A in the tower 16 falls below the height at which the sensor 32 is positioned, the sensor will trip and activate the reset light 68 and disconnect the power to switch 50. This will, in turn, disable the tower heater 20 and the cabinet heaters 62. The sensor 32 is preferably located approximately one foot (25.5 cm) from the base of the tower 16.

During normal operation, the main cabinet power selector switch 50 is turned on and the cabinet heaters 62 as well as the saturation tower heater 20 are actuated. The liquid level at this time in the saturation tower 16 should be approximately two-thirds full. The sensor 32 is also energized through the relay coil 66. If the sensor is in the form of a proximity sensor, and if the liquid level should now for some reason decrease from the two-thirds setting to a level below the position of the proximity sensor, due to operator error or a system malfunction, the sensor 32 will signal the relay coil 66 which will interrupt power to the cabinet heaters 52 and saturation tower heater 20. At the same time the system reset light 68 will be illuminated. Similarly, if a temperature sensor is utilized, if the tower wall temperature increases above a predetermined level due to a lack of liquid in the tower, the tower heater and cabinet heaters will be de-energized and the reset light will be illuminated.

In order to reset the system, the water level in the saturation tower 16 will have to be raised, which will also cool down the tower walls. Once this is accomplished, the system reset pushbuttons 38 can be depressed. At this time, the cabinet heaters 62 will be energized again and the system reset light 68 will de-illuminate. At the same time, the saturation tower heater 20 will also be energized. The system is now completely reset for operation.

The subject invention thus provides a control device for an air saturation tower of a corrosion testing apparatus. Should the water level be insufficient in the saturation or bubble tower due to a leaky water inlet tube, an empty water reservoir or operator error or neglect, the control device will autolmatically shut off the electrical power to the cabinet heaters and the saturation tower heater. The systems cannot be restarted until a proper water level is obtained in the saturation tower. A melting of the saturation tower or other heat damage thereto is thus prevented due to an over-temperature condition such as caused by an inadequate amount of water being held in the tower.

The invention has been described with reference to preferred embodiments. Obviously, alterations and modifications will occur to others upon the reading and understanding of this specification. It is intended to include all such modifications and alterations insofar as they come within the scope of the appended claims or the equivalents thereof.

Having thus described the invention, it is now claimed:

1. A control device for a corrosion testing apparatus, comprising:
   an airtight air saturation tower which is adapted to contain a liquid;
   a heater provided in said tower to heat the liquid;
   a sensor means provided adjacent a wall of said tower for sensing the presence of said liquid in said tower;
   a frame means for supporting said tower and a holder means for supporting said sensor means, said holder means being selectively movable on said frame means so that said sensor means can be selectively moved in relation to said tower; and
   a control means for shutting off said heater when said sensor means detects an absence of liquid in said tower.

2. The device of claim 1 wherein said holder means includes a mounting bracket and said frame means includes a plurality of tie rods secured between top and bottom plates positioned on respective ends of said tower, said bracket being slidably attached to at least one of said tie rods.

3. The device of claim 1 wherein said control means comprises a relay coil and a safety shut down warning light which are electrically connected to said sensor means.

4. The device of claim 3 wherein said control means further comprises a reset switch electrically connected to said safety shut down warning light, said sensor means and said relay coil.

5. The device of claim 1 wherein said tower is adapted to contain a corrosive liquid.

6. The device of claim 5 wherein said tower is made from a transparent plastic material for corrosion resistance and easy inspection.

7. The device of claim 1 wherein said sensor means is a non-invasive sensor which does not extend into said tower.

8. The device of claim 1 wherein said sensor means is a proximity sensor.

9. An over-temperature control device for an air saturation tower of a corrosion testing apparatus, comprising:
   an airtight air saturation tower which is adapted to contain a liquid, said tower having a bottom wall and side walls;
   a heater extending upwardly in said tower from said tower bottom wall to heat said liquid;
   a non-invasive temperature sensor positioned adjacent said tower such that a sensing face of said sensor is in physical contact with a tower wall, said sensor being responsive to the temperature of said tower wall and adapted to signal when said wall temperature becomes excessive, said temperature sensor being electrically connected to said heater whereby if said wall temperature becomes excessive said heater will be automatically disconnected;
   a frame means for holding said tower; and,
   a holder means for supporting said sensor, said holder means being selectively movable on said frame means, said holder means including a mounting bracket and said frame means including a plurality of tie rods secured between top and bottom plates positioned on respective ends of said tower, said bracket being slidably secured to at least one of said tie rods.

10. The device of claim 9 further comprises a control means comprising:
    a safety shut down warning light;

a relay coil for shutting off said heater when said temperature sensor signals; and, a reset switch, said warning light, said relay coil and said reset switch being electrically connected to said temperature sensor.

11. A control device for an air saturation tower of a corrosion testing apparatus, comprising:

an airtight air saturation tower which is adapted to contain a corrosive liquid, said tower having a bottom wall and said walls;

a heater provided in said tower to heat said liquid therein;

a temperature control for controlling normal operation of said heater;

a proximity sensor positioned adjacent a wall of said tower and not extending into said tower, said sensor being disposed to sense an abnormal condition in said tower;

a frame means for holding said tower and a holder means for supporting said sensor, said holder means being selectively securable to said frame means:

a safety shut down warning means associated with said sensor; and, a switching means electrically connected to said sensor and to said safety shut down warning means to actuate the latter when said switching means deenergizes said heater due to a signal sent by said sensor.

12. The device of claim 11 wherein said proximity sensor senses the presence of liquid in said tower adjacent said sensor.

13. The device of claim 12 wherein said heater extends upwardly from a bottom of said tower and wherein said sensor is positioned approximately one foot (25.5 cm) away from said bottom of said tower.

14. The device of claim 11 wherein said holder means includes a mounting bracket and said frame means includes a plurality of tie rods secured between top and bottom plates positioned on respective ends of said tower, said bracket being slidably secured to at least one of said tie rods.

* * * * *